(12) United States Patent
Huang et al.

(10) Patent No.: US 8,247,001 B2
(45) Date of Patent: Aug. 21, 2012

(54) ANTI-OBESITY PRODUCT AND ITS METHOD OF PREPARATION

(75) Inventors: Bendong Huang, Guangzhou (CN); Nanming Chen, Guangdong Province (CN); Edward Duncan Blair, Cambridge (GB)

(73) Assignee: Chongquing Institute of Ecological Materia Medica Co. Ltd, Nanping, Chongquin (CN)

( * ) Notice: Subject to any disclaimer, the term of this patent is extended or adjusted under 35 U.S.C. 154(b) by 12 days.

(21) Appl. No.: 12/373,093

(22) PCT Filed: Jul. 9, 2007

(86) PCT No.: PCT/GB2007/002548
§ 371 (c)(1),
(2), (4) Date: Jun. 29, 2009

(87) PCT Pub. No.: WO2008/007063
PCT Pub. Date: Jan. 17, 2008

(65) Prior Publication Data
US 2010/0021568 A1 Jan. 28, 2010

(30) Foreign Application Priority Data
Jul. 10, 2006 (GB) .................................. 0613683.2

(51) Int. Cl.
*A01N 65/00* (2009.01)

(52) U.S. Cl. ....................................................... 424/725
(58) Field of Classification Search .................... None
See application file for complete search history.

(56) References Cited

U.S. PATENT DOCUMENTS
2004/0044067 A1 * 3/2004 Pan ............................... 514/455

FOREIGN PATENT DOCUMENTS
| CN | 20051036857 | 8/2005 |
| EP | 1256350 A1 | 11/2002 |
| EP | 1552838 A1 | 7/2005 |
| JP | 19880300983 | 11/1988 |

OTHER PUBLICATIONS

Yamamoto, M., et al.; Anti-obesity effects of lipase inhibitor CT-II, an extract from edible herbs, Nomame Herba, on rats fed a high-fat diet; International Journal of Obesity; Jun. 1, 2000; pp. 758-764; vol. 24 No. 6; Newman Publishing; London, GB.

Li, X-E, et al., Effects of casia seeds protein and anthraquinoneglycoside on blood fat of rats with hyperlipemia; Chinese Journal of Clinical Rehabilitation 200406 China; Jun. 2004; pp. 3694-3695; vol. 8, No. 18.

Zhang, X-L, et al.; Purification technology of anthraquinoneaglycone from *Cassia obtusifolia* seeds by macroporous adsorption resin; Chinese Traditional and Herbal Drugs 200610 China; Oct. 2006; pp. 1482-1486; vol. 37, No. 10.

Wong, Sui-Ming, et al.; Anthraquinone Glycosides From The Seeds of *Cassia tora*; Phytochemistry; 1989; pp. 211-214; vol. 28, No. 1; Great Britain.

Xiaohua, W. et al.; Pharmacological Study on "Zishen Huayu Fang" on Treatment or Mesangial Proliferative Glomerulonephritis in Rats; Journal of Chinese Medicinal Materials; Apr. 2004; pp. 281-284; vol. 27, No. 4.

Jian-Zhuang, Yang et al.; Dose-effect relationship of cassia seed decoction with its inhibition on increased body mass in nutritional obese rats; Chinese Journal of Clinical Rehabilitation; Aug. 21, 2005; pp. 226-228; vol. 9, No. 31.

Yingming, Guan et al.; Yishou Jiangzhi (De-Blood-Lipid) Tablets in the Treatment of Hyperlipemia; Journal of Traditional Chinese Medicine; Sep. 1995; pp. 178-179; vol. 15, No. 3.

Ianiri G.; A randomized, double blind, placebo controlled study Chitosano (Ultra)+ Cassia Nomame in overweight and mildly obese individuals; Progress In Nutrition; 2002; pp. 147-150; vol. 4, No. 2.

* cited by examiner

*Primary Examiner* — Michael Meller
(74) *Attorney, Agent, or Firm* — Dickinson Wright PLLC

(57) ABSTRACT

The present invention relates to compositions comprising one or more anthraquinones for use in the treatment of obesity and related metabolic and liver disease. More particularly it relates to a plant extract fraction rich in anthraquinones including both anthraquinone glycosides and anthraquinone aglycones obtainable from a member of the Leguminosae family, more particularly *Cassia* seeds. It also relates to a method of obtaining a plant extract fraction rich in anthraquinones.

14 Claims, 12 Drawing Sheets

1 Aurantion-obtusin
2 Obtusifolin
3 Sample 1
4 Sample 2
5 Sample 3
6 Sample 4
7 Aurantion-obtusin
8 Obtusifolin 1 Aurantion-obtusin
2 Obtusifolin
3 Sample 1
4 Sample 2
5 Sample 3
6 Sample 4
7 Aurantion-obtusin
8 Obtusifolin

* = statistically significant difference from "Control – HFD" (P>0.05).

FIG 8A
FIG 8B
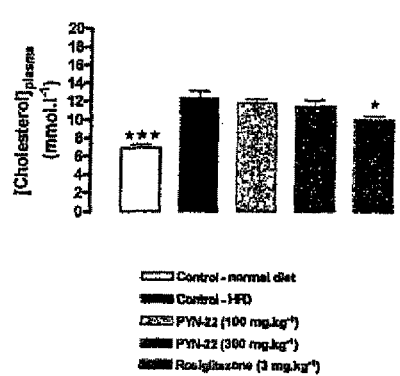
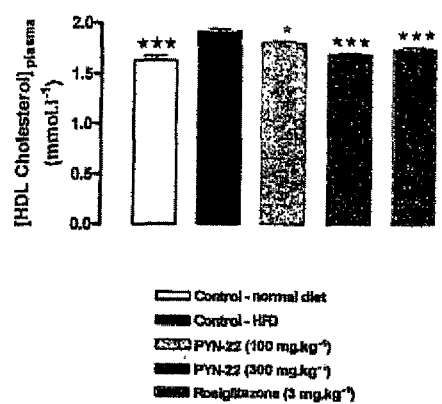
\* = statistically significant difference from "Control – HFD" (P<0.05).
\*\*\* = high statistically significant difference from "Control – HFD" (P<0.01).

* = statistically significant difference from "Control – HFD" (P<0.05).
*** = high statistically significant difference from "Control – HFD" (P<0.01).

\* = statistically significant difference from "Control – HFD" ($P<0.05$).
\*\*\* = high statistically significant difference from "Control – HFD" ($P<0.01$).

\* = statistically significant difference from "Control – HFD" (P<0.05).
\*\* = strong statistically significant difference from "Control – HFD" (P<0.02).

ANTI-OBESITY PRODUCT AND ITS METHOD OF PREPARATION

TECHNICAL FIELD

The present invention relates to compositions comprising one or more anthraquinones for use in the treatment of obesity, metabolic disease, or liver disease.

More particularly it relates to a plant extract fraction rich in anthraquinones including both anthraquinone glycosides (major anthraquinone component, typically accounting for from 0.8-1.6% by weight of the starting material) and anthraquinone aglycones (minor anthraquinone component, accounting for up to 0.2% by weight of the starting material) obtainable from a member of the Leguminosae family, more particularly Cassia seeds. It also relates to a method of obtaining a plant extract fraction rich in anthraquinones.

BACKGROUND ART

Obesity and their associated metabolic and liver diseases are a global problem. In the Western world, obesity has become a most pressing health problem, with over 20% of the population effected. In America 65% of adults (127 million) are overweight or obese and healthcare costs for obesity and obesity-related conditions are estimated to amount to $100 billion.

The problem is growing in Europe. In the UK about 43% of men and 34% of women are overweight with a further 22% of men and 23% of women being clinically obese. There is a rising level of premature obesity in children and obesity is increasing in the developing world.

Anti-obesity medicines are usually divided into categories by mechanisms of action, namely those which:

(1) Reduce the feeling of hunger or suppress appetite through the central brain;
(2) Inhibit fat absorption through affecting the digestive system;
(3) Increase the energy consumption through capillary ending mechanism; and
(4) Stimulate the metabolic function of the capillary ending of adipose tissues to decrease the fat quantity or reduce synthesis of triglyceride.

Sibutramine and Orlistat are two anti-obesity drugs approved by the America FDA. These two drugs have the largest market shares in weight-loss medicines in the world.

The applicant has sought a natural solution to the problem of obesity.

Although Yang et al (Chinese Journal of Clinical Rehabilitation, 21 Aug. 2005 Vol. 9, No. 31) observed that a decoction (water extract) of Cassia-seed inhibited the weight gain, in rats with nutritional obesity, the active compounds or fraction of Cassia seeds which related to the activity of inhibiting the weight gain has not previously been identified.

Other prior art includes:

J. Natural products, 1990, Vol. 53, No. 3, pp. 630-633 which discloses a hexane extraction followed by a methanolic fractionation of Cassia seeds to obtain sub-fractions which showed activity as inhibitors of platelet aggregation. The three active fractions contained respectively gluco-obtusifolin, gluco aurantio-obtusifolin and gluco-chrysobtusin.

CN1733679 which discloses a method of extracting anthroquinone analog compounds from Cassia seeds. The compounds extracted are anti-hyperglycemic ingredients.

JP0214915 discloses aldose reductase inhibitors containing anthraquinone compounds used in treating complications in diabetes.

Arch. Pharm. Res. Vol. 19, No. 4, p 302-306, 1996 discloses NMR assignments of anthraquinones isolated from Cassia tora.

J Chinese Medicinal Materials, 2004, vol. 24 pp. 758-764 discloses a water extract of Cassiae seeds. It reports that obese rats showed weight loss, and metabolism of glucose and lipid.

International Journal of Obesity, 2000, vol. 24, pp. 758-764 discloses an extract CT-II of Cassia mimosoides L var nomame showed an inhibitory effect on lipase. The extract was a fraction of an aqueous ethanolic extract.

J. Traditional Chinese Med, 1995, vol. 15, no. 3 pp. 178/9 discloses a trial of a 5 herb mix including Cassia Tora in the treatment of hyperlipemia. The mix was shown to reduce serum cholesterol and triglycerides as well as bodyweight.

Progress in nutrition, 4, 2, 147-150, 2002 reports on a trial of Chitosano and Cassia Noname var Mimosoides on obese patients.

BE 1009545 discloses food supplements for slimming purposes comprising a combination of at least three vegetable extracts from a selection of seven, one of which is senna pods (Cassia sp).

The applicant has identified Chinese Cassia seeds as a promising candidate and has, for the first time, carried out systematic studies on Cassia seeds in accordance with the regulatory requirements of the Chinese Food and Drug Administration (CFDA) in the following areas:

1. Botany and Pharmacognosy
2. Phytochemistry
3. Pharmacology and Toxicology
4. Pharmaceutical processes
5. Analytical chemistry
6. Pharmaceutics The botanical terms used herein are intended to have the meanings as used by the FDA in their directive "Guidance for Industry—Botanical Drug Products" (June 2004) which directive is incorporated by reference. It will, however, by understood by persons skilled in the art that in different countries different terminology may be used. Reference to the FDA guidance terminology is used for consistency and should not be taken to be limiting. Thus, differing but equivalent terms used by, for example, the CFDA or EMEA in their Guidelines on Quality of Herbal Medicinal Products/Traditional Herbal Medicinal Products (CHMP/THMP adopted March 2006), will be understood by the skilled person to be encompassed by the terms used herein.

DISCLOSURE OF THE INVENTION

According to a first aspect of the present invention there is provided plant extract, from a member of the Leguminosae family, comprising by analysis:

i) at least 1% aurantio-obtusin (by hplc analysis);
ii) at least 0.05% obtusifolin (by hplc analysis); and
iii) at least 10% total anthraquinone (by UV spectroscopy).

Preferably the plant from the Leguminosae family is from a Cassia spp.

Preferably the Cassia spp. is selected from:
1. Cassia obtusifolia, or
2. Cassia tora although other Cassia species including Cassia occidentalis L might be used. Most preferred is Cassia obtusifolia.

Preferably the plant material used is the seed.

The preferred plant extract can be defined by reference to markers. The preferred markers are aurantio-obtusin and obtusifolin.

Preferably, aurantio-obtusin is present in an amount (by HPLC analysis) that constitutes at least 1% of the extract.

More preferably the content of aurantio-obtusin, measured as and calculated on the basis of the total aglycone, after acid hydrolysis, constitutes at least 2%, increasing in integers of 1%, through 3%, 4% to most preferably at least 5% and may increase further through 6%, 7%, 8%, and 9% to as much as 10% or higher.

Preferably, obtusifolin is present in an amount (by HPLC analysis) that constitutes at least 0.1%, of the extract. More preferably the content of obtusifolin, measured as and calculated on the basis of the total aglycone after acid hydrolysis, constitutes at least 0.2%, increasing in integers of 0.1%, through 0.3%, 0.4%, to 0.5% and may increase further though 0.6% and 0.7% to as much as 0.8% or higher.

This can be determined using HPLC and/or methodology as described in the detailed description.

The preferred composition comprises a defined ratio mix of the markers
1. Aurantio-obtusin; and
2. Obtusifolin.

Most preferably the two markers are present in a ratio of aurantio-obtusin:obtusifolin of between 5:1 to 30:1, more preferably 5:1 to 16:1 and most preferably between 8:1 and 16:1. Most preferred is a ratio of greater than 8:1.

Such a ratio of markers may differ from that naturally found in the plant as can be seen from Example 1 which discloses a method for obtaining and purifying the respective markers from an ethanolic extract. It will be noted that the aurantio-obtusin is obtained from fraction A at levels of eight times that of the obtusifolin found in fraction B. In contrast, the present invention preferably uses a fraction with higher relative proportions of aurantio-obtusin to obtusifolin. (Preferably greater than 8:1, and most preferably between 8:1 and 16:1).

Preferably the extract comprises a total anthraquinone content of at least 25%, more preferably at least 30%, through 35%, 40%, 45% to 50% or more (by UV spectrometry).

The anthraquinones associated with *Cassia* spp are illustrated in the tables 1 and 2 below:

TABLE 1

Table 1 Chemical components of anthraquinones from *Cassia obtusifolia* L. and *Cassia tora* L.

| *Cassia obtusifolia* | | *Cassia tora* | |
|---|---|---|---|
| Emodin | 1 | | 1 |
| Chrysophanol | 2 | | 2 |
| Rhein | 3 | | 3 |
| Physcion | 4 | | 4 |
| Ale-emodin | 5 | | 5 |
| Chrysarobin | 6 | | 6 |
| Chrysophanic acid anthrone | 7 | | 7 |
| Obtusifolin | 8 | | 10 |
| Obtusin | 9 | | 11 |
| Chryso-obtusin | 10 | Chrysophanol-1-β-geniobioside | 28 |
| Aurantio-obtusin | 11 | 1-[(β-D-glucopyranosyl-(1→ 3)-O- | 29 |
| Questin | 12 | β-D- | |
| Gluco-obtusifolin | 13 | glucopyranosyl(1→ 6) O-β-D-glucopyranosyl)oxy]-8-hydroxy-3 methyl-9,10-anthraquinone | |
| Gluco-obtusin | 14 | 1-[(β-D-glucopyranosyl-(1→ 6)-O- | 30 |
| Gluco-aurantioobtusin | 15 | β-D- | |
| 1-Demethyl auratioobtusin | 16 | glucopyranosyl(1→ 3) O-β-D-glucopyranosyl(1→ 6)-O-β-D-glucopyranosyl)oxy]-8-hydroxy-3 methyl-9,10-anthraquinone | |
| 1-Denethylobtusin | 17 | 2-(β-D-glucopyranosyloxy-8-hydroxy-1-methoxy-3 methyl-9,10-anthraquinone | 31 |
| 1-Demethyl chryso-obtusin | 18 | Alaterin-2-O-β-D-glucopyranoside | 32 |
| Chrysophanol 10, 10-bianthrone | 19 | | |
| Echinul polydric anthrone-8-O-D-glucopyranoside | 20 | | |
| Alaternin-1-O-β-D-glucopyranoside | 21 | | |
| Emodin-6-glucoside | 22 | | |
| Emodin anthrone | 23 | | |
| Chryso obtusin-2-O-β-D-glucopyranoside | 24 | | |
| Chryscion 8-O-D-glucopyranoside | 25 | | |
| 1,3-dihydroxy-6-methoxy-7-methyl-anthraquinone | 26 | | |
| 1-hydroxy-3,7-diformyl-anthraquinone | 27 | | |

TABLE 2

Table 2. List of chemical structural formula of partial anthraquinones from Cassia Seeds

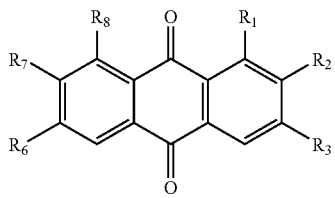

| No. | $R_1$ | $R_2$ | $R_3$ | $R_6$ | $R_7$ | $R_8$ |
|---|---|---|---|---|---|---|
| 1 | OH | H | $CH_3$ | OH | H | OH |
| 2 | OH | H | $CH_3$ | H | H | OH |
| 3 | OH | H | COOH | H | H | OH |

TABLE 2-continued

Table 2. List of chemical structural formula of
partial anthraquinones from Cassia Seeds

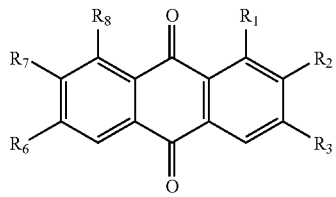

| No. | $R_1$ | $R_2$ | $R_3$ | $R_6$ | $R_7$ | $R_8$ |
|---|---|---|---|---|---|---|
| 4 | OH | H | $CH_3$ | $OCH_3$ | H | OH |
| 5 | OH | H | $CH_2OH$ | H | H | OH |
| 8 | $OCH_3$ | OH | $CH_3$ | H | H | OH |
| 9 | $OCH_3$ | OH | $CH_3$ | $OCH_3$ | $OCH_3$ | OH |
| 10 | $OCH_3$ | OH | $CH_3$ | $OCH_3$ | $OCH_3$ | $OCH_3$ |
| 11 | $OCH_3$ | OH | $CH_3$ | OH | $OCH_3$ | OH |
| 12 | OH | H | $CH_3$ | OH | H | $OCH_3$ |
| 16 | OH | OH | $CH_3$ | OH | $OCH_3$ | OH |
| 17 | OH | OH | $CH_3$ | $OCH_3$ | $OCH_3$ | OH |
| 18 | OH | OH | $CH_3$ | $OCH_3$ | $OCH_3$ | $OCH_3$ |
| 21 | O-glu | OH | $CH_3$ | OH | H | OH |
| 22 | OH | H | $CH_3$ | O-glu | H | OH |
| 24 | $OCH_3$ | O-glu | $CH_3$ | $OCH_3$ | $OCH_3$ | $OCH_3$ |
| 25 | OH | H | $CH_3$ | $OCH_3$ | H | O-glu |
| 26 | OH | H | OH | $OCH_3$ | $CH_3$ | H |
| 27 | OH | H | CHO | H | CHO | H |
| 28 | O-gen | H | $CH_3$ | H | H | OH |
| 29 | O-① | H | $CH_3$ | H | H | OH |
| 30 | O-② | H | $CH_3$ | H | H | OH |
| 31 | $OCH_3$ | O-glu | $CH_3$ | H | H | OH |
| 32 | OH | O-glu | $CH_3$ | OH | H | OH |

Preferably the extract is an extract which has been purified such that it has been purified by at least a factor of 10, compared to the dry weight of the starting materials, and more preferably at least a factor of 25, through 50, 75 and 100. Thus, preferably it contains less than 10% more preferably still less than 4% through 2% and most preferably less than 1% by weight of the starting material.

The extract obtained is primarily designed as a Botanical Drug Substance (BDS) with the intended use as an active pharmaceutical ingredient (API) to be made into a pharmaceutical dosage form or Botanical Drug. Alternatively the extract may be used as an ingredient of a dietary supplement or health foodstuff where its inclusion may be to bring about a therapeutic or cosmetic effect.

In order to obtain a characterized extract according to the invention the Applicant has had to overcome a number of problems including:
 1. Ensuring quality assurance, QA, and quality control, QC, of the starting raw material;
 2. Developing novel extraction and purification processes;
 3. Defining the specification of the extract;
 4. Developing appropriate analytical methodology specific to both the raw material and the extract;
 5. Identifying relevant chemical markers;
 6. Producing standard reference chemicals;
 7. Identifying the active fraction and it's characteristics;
 8. Determining the activity so as to produce an appropriate final dosage form; and
 9. Determining the toxicity of the extract.

When the extract is used as a BDS, it is preferably formulated for oral delivery. It may be taken in such forms as a powder, solution, suspension, tablet, lozenge, granule or capsule. A capsule dosage form containing a dried extract has been shown to exhibit therapeutic activity.

The extract preferably takes the form of a dried extract powder, which may be taken as a daily dose in an amount of from 50-5,000 mg. A typical adult dose will be 500 mg (equivalent to a daily intake of 50 g of raw material).

Preferably the plant species is a *Cassia* spp selected from:
 1. *Cassia obtusifolia*; or
 2. *Cassia tora*.

Most preferably the plant species is *Cassia obtusifolia* and more particularly still *Cassia obtusifolia* grown in the habitat of Hubei Provence of China since plant material from this region has been found by the applicant to contain a higher percentage of aurantio-obtusin, measured as and calculated on the basis of the total aglycone after acid hydrolysis, than plant material from other regions (greater than 0.06%, typically around 0.08%). Alternatively, the seeds of *C. obtusifolia* grown in Shanxi and Anhui Provinces may also be used.

The preferred plant material is seed.

Preferably the fraction is obtained by way of an ethanolic extraction, most preferably a reflux extraction as such a method gives significantly higher concentrations of the marker compounds and total anthraquinones than alternative methods.

Preferably the method includes steps to remove:
 i) Any lipo-soluble oils; and
 ii) Water soluble gums.

This may comprise respectively:
 i) A separation with super-speed centrifugation or partitioning with lipo-soluble solvents, such as, for example petroleum ether, chloroform, etc; and
 ii) Washing in water and/or a low concentration of ethanol. (Less than 30% by volume).

Preferably a resin absorption separation and purification process is conducted using a macroporus resin column. The favored macroporous resin is a non-polar styrol copolymer resin, such as, for example (D101) produced by Tianjin Agricultural Chemical Corp. Ltd, Resin Branch. This has the following specifications:
 Product Name: Macroporous Resin
 Chemical Name: Styrol Copolymer
 Brand (Type): Yuanhang Brand (D101)
 Structure: PSD
 Appearance: Milky white or light yellow opaque global granule
 Polarity: Non-polarity
 Specific surface area: 400 $m^2/g$
 Grain size: 20-60 mesh≧90%
 Moisture: 65-75%
 Average pore diameter: 0.0301 μm
 Porosity: 70.5%
 Pore volume: 1.6824 ml/g
 Wet true density: 1.1778 $g/cm^3$
 Apparent density: 0.65-0.70 g/ml
 Dry density: 0.3475 $g/cm^3$
 Skeleton density: 0.8369 $g/cm^3$ Other advantageous process conditions will be apparent from the supporting data given in the detailed description. These include:
 1. The use of a 50-80% ethanolic solution for extraction;
 2. The optimization of reflux extraction conditions;
 3. The pre-treatment process for column purification;
 4. The selection of a preferred macroporous resin together with selected column dynamics: e.g. height ratio of the resin bed should be 1:5-1:50;
 5. The control of elution conditions to remove impurities e.g. volume/concentration/speed e.g. Elute with 2 BV (bed volume) of distilled water, and then with 1-8 BV of 20% ethanol at a speed of 1-5 BV/h; and 6. The control of elution conditions to control anthroquinone separation e.g. Elute with 1-10 BV of 70% ethanol at the speed 1-5 BV/h, collect the ethanol eluent.

According to further aspects of the invention there are provided a Botanical Product (including a food, drug or cosmetic), such as, for example a Botanical Drug Product, Botanical Drug, Botanical drug substance, Cosmetic, or Dietary supplement. The Botanical Drug preferably takes the form of an oral dosage form, preferably delivered as a dry powdered extract in a capsule.

According to yet further aspects of the invention there are provide the use of a plant extract, from a Leguminosae family, in the manufacture of a medicament for the treatment of obesity, metabolic disease or liver disease; the use of a plant extract, from a Leguminosae family, in the manufacture of a cosmetic preparation for the treatment of obesity and the use of a plant extract, from a Leguminosae family, in the manufacture of a functional food or dietary supplement.

According to still yet further aspects of the invention there are provided a method for the treatment of obesity, metabolic disease or liver disease comprising administering a plant extract, from a Leguminosae family; a method for the cosmetic treatment of obesity comprising administering a plant extract, from a Leguminosae family; and a method for supporting weight loss comprising administering a functional food or dietary supplement comprising a plant extract, from a Leguminosae family.

The various aspect of the invention will be further described, by way of example only, with reference to the following Figures and Examples:

BRIEF DESCRIPTION OF THE DRAWINGS

FIG. 5A is a graph showing the effect of PYN22 on blood cholesterol—total cholesterol;

FIG. 8B is a graph showing the effect of PYN22 on blood cholesterol—HDL-cholesterol;

Figure 1:
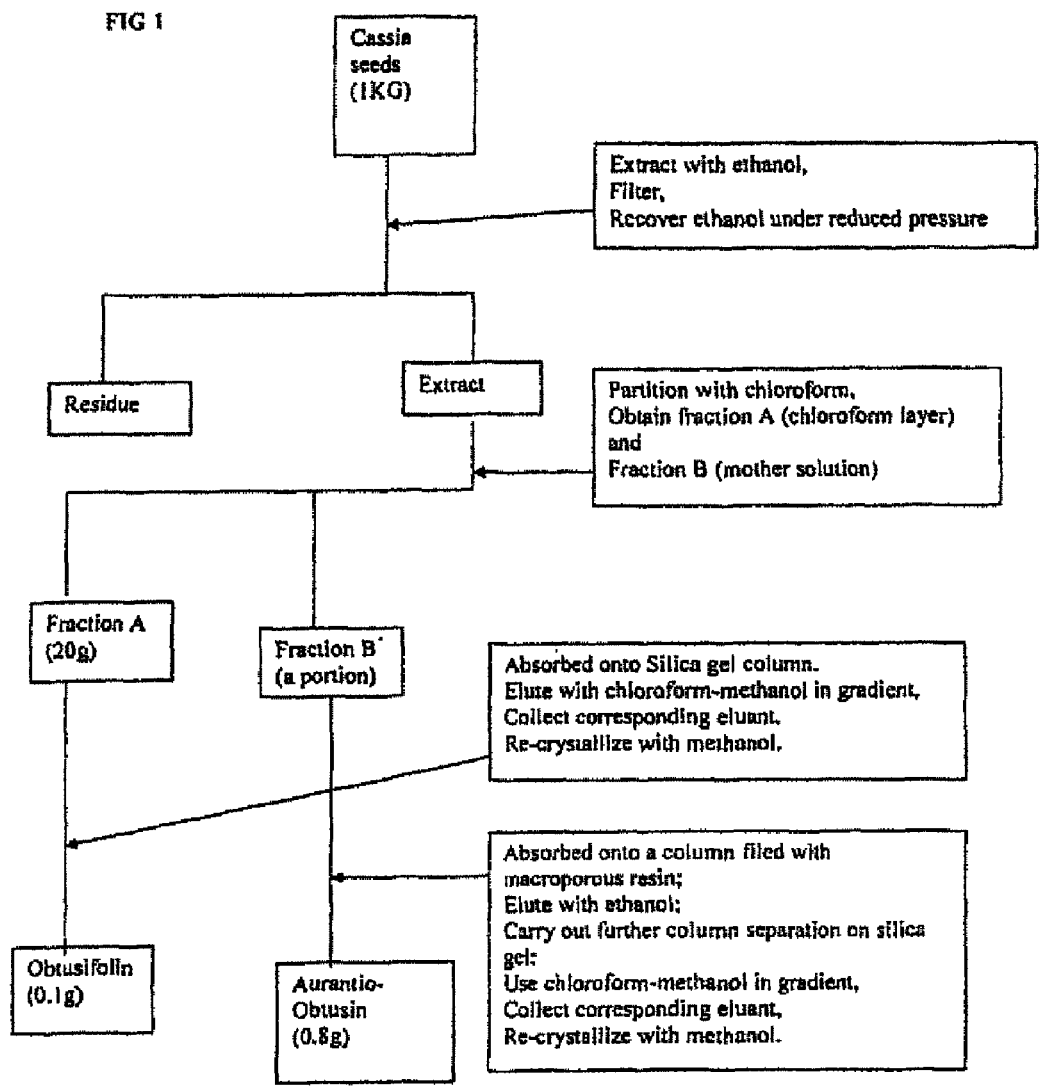
FIG. 1 is a flow diagram showing a method of obtaining pure samples of the markers aurantio-obtusin and obtusifolin from *Cassia* seed.

DETAILED DESCRIPTION 1.0 Starting Materials
1.1 Background

*Cassia* seeds (both *Cassia tora* L. and *Cassia obtusifolia* L.) contain anthraquinones, naphtha-pyrones, fatty acids, amino acids and inorganic elements. The main constituents are anthraquinones including 0.8-1.6% anthraquinone glycosides and 0.06-0.2% anthraquinone aglycones.

*Cassia* seeds usually refer to mature dried seeds of *Cassia tora* L. and *Cassia obtusifolia* and are widely available. *Cassia occidentalis* on the other hand is only used in some local areas of southern China.

According to the distribution of the plants, *Cassia tora* L. is distributed in the provinces south of the Yangtze River, and can not be cultivated in the northern area as it is not able to bear flowers or fruits. On the other hand *Cassia obtusifolia* L. can grow both in the north and south. The literature indicates that in ancient time, *Cassia* seeds were from the above three species.

Research on the chemical components of *Cassia*, has primarily been carried out by Japanese scientists with Japanese *Cassia* seeds. Some of the prominent chemicals isolated from Japanese *Cassia*, e.g. rhein and aloe-emodin, don't seem to exist in Chinese *Cassia* seeds. Scientists have so far paid very little attention to the chemical profile of Chinese *Cassia* seeds, except the knowledge of the existence of a few frequently occurring Rheum anthraquinones. The active component of, and chemicals specific to Chinese *Cassia* seed, are as yet to be identified. At the moment the quality control method for raw material of *Cassia* seeds and its preparation is based on the determination of the content of Chrysophanol and total anthraquinones. The former ubiquitously exists in many medicinal plants containing anthraquinone derivatives while the measurement of the latter is even less specific.

Through a systematic phytochemical study on *Cassia* seeds, the applicant has determined that plant material from North China mainly contained chrysophanol, physcion, obtusifolin, emodin, and aruantio-obtusin. Two of them, aruantio-obtusin and obtusifolin seem to be the characteristic chemicals of Chinese *Cassia* seeds, while aruantio-obtusin was found to be the most prominent chemical in those fractions which produced a marked weight loss effect.

1.2 Selection of the Raw Materials

Based on the applicants' research, the amounts (by weight) of the active constituents in *Cassia tora* were found to be lower than those in *Cassia obtusifolia*. So *Cassia obtusifolia* was selected for further investigation.

There are many places producing *Cassia* species and the contents of the anthraquinones and aurantio-obtusin varied significantly. The applicant investigated the samples from Guangxi, Anhui and Hubei provinces in order to identify a most appropriate production site and to ensure the consistent quality of the raw materials.

The raw materials from the above locations were quantified for their content of the anthraquinones and aurantio-obtusin, measured as, and calculated on the basis of, the total aglycone after acid hydrolysis, by UV spectrophotometry and HPLC methods, respectively.

The results of the investigation are illustrated in Table 3 below:

TABLE 3

Table 3 Quantitative assay for raw materials from different locations

| Raw material Location | Anthraquinones Mean % | Aurantio-obtusin Mean % |
|---|---|---|
| Guangxi | 0.8 | 0.051 |
| Anhui | 1.1 | 0.071 |
| Hubei | 1.4 | 0.080 |

From table 3 it will be noted that the chemical content of the raw materials varied with location. Based on the results applicant selected the *Cassia obtusifolia* raw materials from Hubei province.

2.0 Compounds

The marker compounds used to characterize the plant extract of the invention are noted below:

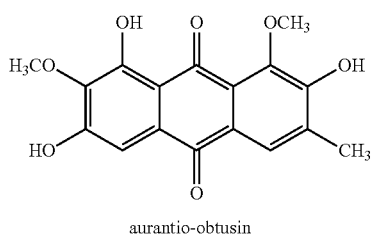

aurantio-obtusin

Registry Number: 67979-25-3
and

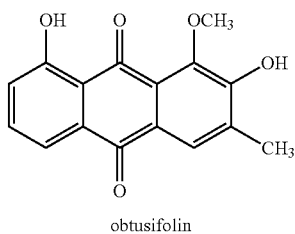

obtusifolin

Registry Number: 477-85-0

3.0 Extraction 3.1 Method of Separation and Purification of Obtusifolin and Aurantio-Obtusin from *Cassia* Seeds Referring to FIG. 1, 1 Kg of cassia seeds were extracted with ethanol. The solution was filtered and the ethanol recovered under reduced pressure leaving a residue and extract (190 g).

The extract was partitioned with chloroform producing a chloroform layer—Fraction A and the mother solution—Fraction B.

Fraction A (20 g) was absorbed onto a silica gel column, eluted with chloroform-methanol in gradient. The corresponding eluent was collected and re-crystallized with methanol. It contained 0.1 g of obtusifolin.

Fraction B was absorbed onto a macroporous resin column and eluted with ethanol. The eluent was further separated on a silica gel column and eluted with chloroform-methanol in gradient. The corresponding eluent was collected and re-crystallized with methanol. It contained 0.8 g of aurantio-obtusin.

3.1.1 Quantitative Assay
3.1.2 Equipments and Materials

HPLC Agilent 1100 Series, diode-array multi wavelength detector.

Methanol and acetonitrile (chromatographic grade), de-ionized water and phosphoric acid (analytical grade).

3.1.3 Method and Result

Chromatography Conditions:
Mobile Phase:

Eluted with methanol-water, methanol-0.1% phosphate, acetonitrile-water, and acetonitrile-0.1% phosphate in gradient, respectively, at different flow rates as shown in Table 4.

TABLE 4

Table 4 The gradient of the mobile phase

| Time | ACN (%) | 0.1% $H_3PO_4$ | FLOW (ml/min) |
|---|---|---|---|
| 0 | 40 | 60 | 0.8 |
| 5 | 50 | 50 | 0.8 |
| 20 | 100 | 0 | 0.8 |

Detection wavelength: with DAD detector, reference standards have the absorption at 278 nm with the reference wavelength at 360 nm.

Chromatographic column: lunar $C_{18}$
Temperature: 25° C.
Running time: 25 mins.

3.1.4 Preparation of the Test Solutions:

Aurantio-obtusin and Obtusifolin reference standards were weighed accurately and put into 10 ml volumetric flasks, respectively. Methanol was added to dissolve the chemicals thoroughly to volume.

Figure 2:
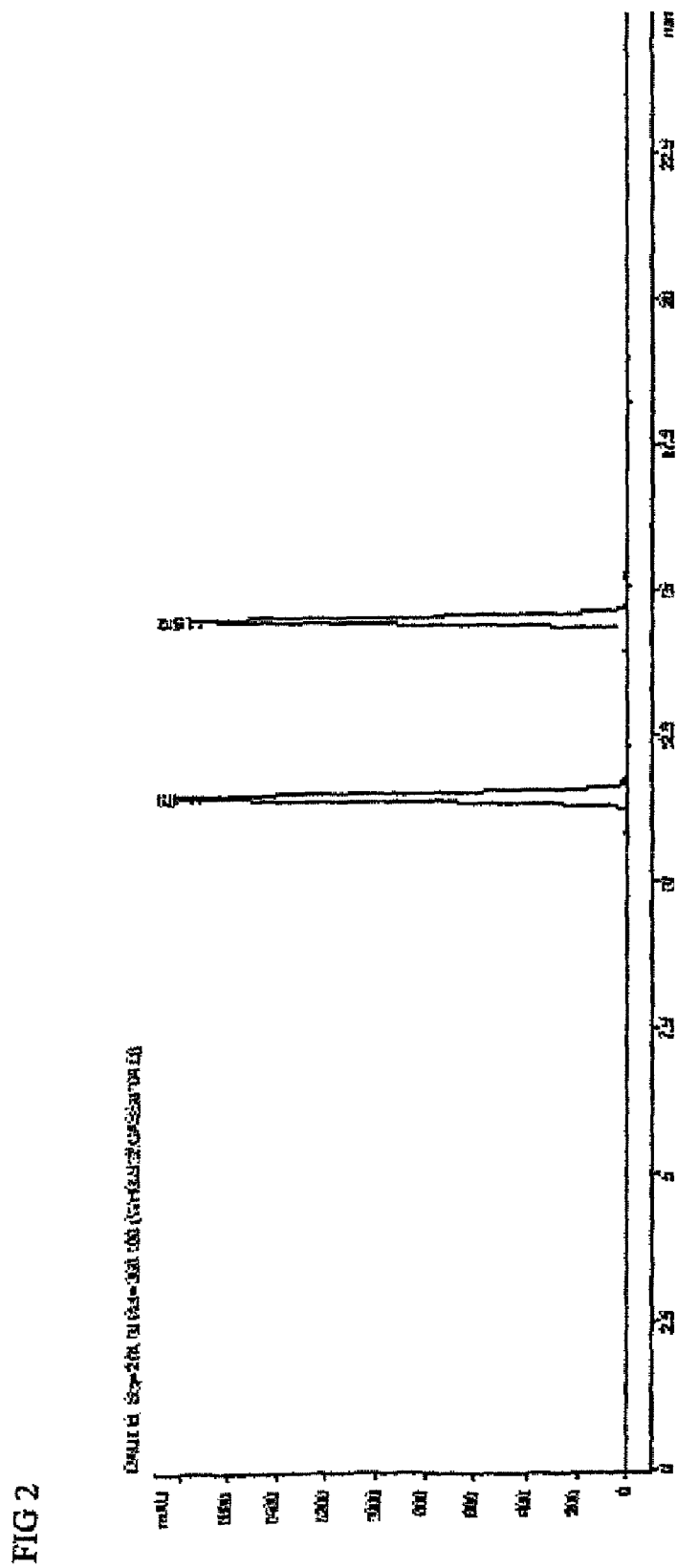
FIG. 2 is an HPLC chromatogram for the markers.

Retention time of Obtusifolin was determined to be 14.512 minutes and Aurantio-obtusin determined to be 11.479 minutes (FIG. 2).

TABLE 5

Table 5 Linear relationship between the HPLC integration peak areas and the reference sample concentrations

| Compounds | Linear Relationship | Correlation Coefficient | Range (μg) |
|---|---|---|---|
| Aurantio-obtusin | Y = 93.3885334x-15.328363 | 0.99999 | 0.092~1.580 |
| Obtusifolin | Y = 123.192564x-3.4891702 | 0.99995 | 0.008~0.580 |

3.2 Preparation of a Plant Extract (Best Mode)

Figure 3:
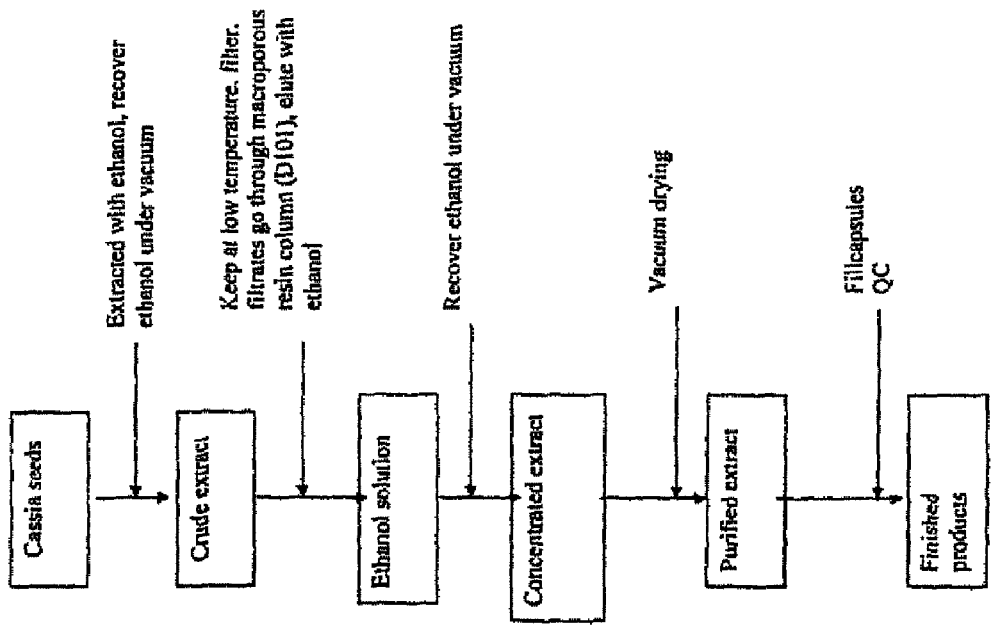
FIG. 3 is a flow diagram showing an extraction method according to one aspect of the invention.

Referring to FIG. 3 there is illustrated the preferred embodiment of a multi-stage process for preparing a plant extract of the invention. It comprises the following steps:

3.2.1 Pulverize *Cassia* seeds (25 Kg) into a coarse powder;
3.2.2 Carry out a reflux extraction with 4-20 folds in volume of 50-80% ethanol for 0.5-3 hours;
3.2.3 Repeat 2-4 times;
3.2.4 Filter and recover ethanol from the solution under vacuum to obtain a crude extract;
3.2.5 Centrifuge the residue to remove any lipo-soluable oils;

3.2.6 Adjust concentration of the extract with distilled water to the ratio 1:1-1:10 (material:solution);

3.2.7 Carry out separation and purification with a column filled with $D_{101}$ Macroporous Resin at the ratio 1:2-20 (diameter:height);

3.2.8 Apply the extract with a quantity of less than 1-4 BV (BV: resin bed volume) to the column with dynamic absorption at the speed of 1-2 BV/h;

3.2.9 Wash with 1-8 BV of water and then with 1-8 BV of 20% ethanol at a speed of 1-5 BV/h;

3.2.10 Elute with 1-10 BV of 70% ethanol at the speed of 1-5 BV/h and collect the ethanol solution;

3.2.11 Recover ethanol and dry the extract under vacuum;

3.2.12 Dissolve the extract in 95% ethanol. Filter and recover the ethanol from the solution to obtain a concentrated extract;

3.2.13 Dry the refined extract under vacuum and then pulverize to give particles of a desired size for filling into capsules (size 1).

The resulting extract is a dark brown powder with a bitter taste. It is soluble in water, ethanol and methanol.

The preferred extraction conditions were selected based on the following findings:

3.3. Selection of Ethanol Concentration

Pilot scale extractions were run at ethanol concentrations ranging from 0% to 80%, in 10% increments, to determine optimum conditions.

Method: Weigh 50 g of *Cassia* seed coarse powder and add 300 ml of ethanol at selected concentrations, respectively. Carry out reflex extraction for 1.5 hours, and repeat 3 times. Filter and adjust the filtrate to 1000 ml.

Measurements: The content of aurantio-obtusin, and the anthroquinone fraction were quantified and yield measures obtained.

The results are illustrated in Table 6 below:

TABLE 6

Table 6. The effect of ethanol concentration on the extraction of *Cassia* seeds

| Ethanol conc | Aurantio-obtusin (mean) | Total anthraquinone (mean) | Yield (mean) |
|---|---|---|---|
| 0 | 0.16 | 5.62 | 8.61 |
| 10 | 0.18 | 5.56 | 8.71 |
| 20 | 0.17 | 5.58 | 7.91 |
| 30 | 0.19 | 6.95 | 8.58 |
| 50 | 0.20 | 8.94 | 8.54 |
| 60 | 0.21 | 9.48 | 8.81 |
| 70 | 0.21 | 9.20 | 8.25 |
| 80 | 0.22 | 9.95 | 8.49 |

From the above it can be seen that the percentage auratonin-obtusin and total anthraquinone content increased with increasing ethanol concentration but extract yield decreased. The optimum combination was at around 60%.

3.4 Selection of Ethanol Extraction Method

Three commonly used ethanol extraction methods: percolation, cold-maceration and reflex extraction, were compared:

Percolation method: Weigh 50 g of *Cassia* seed coarse powder and add 100 ml of 60% ethanol for 12 hours. Percolate with 500 ml ethanol and collect the solution, adjust the volume with ethanol to 1000 ml.

Cold-maceration: Weigh 50 g of *Cassia* seed coarse powder and add 100 ml of 60% ethanol to macerate for 12 hours. Filter the solution under vacuum. Add ethanol 250 ml to the residue and macerate for another 12 hours. Filter the solution under vacuum. Combine the two filtrates. Adjust the solution with the solvent to 1000 ml.

Reflux extraction: Weigh 50 g of *Cassia* seed coarse powder and add 300 ml of 60% ethanol and carry out reflux extraction for 1.5 hours. Add 250 ml ethanol and carry out the extraction for another 1.0 hour. Combine the two filtrates and adjust the solution with the solvent to the volume (1000 ml).

The results are as illustrated in Table 7 below:

TABLE 7

Table 7 Effect of different methods on the extraction of *Cassia* seeds

| Extraction method | Aurantio-obtusin | Anthraquinone | Yield |
|---|---|---|---|
| Percolation | 0.38 | 2.84 | 8.37 |
| Maceration | 0.23 | 1.48 | 5.12 |
| Reflux | 0.86 | 5.92 | 23.47 |

Reflux extraction resulted in significantly higher concentrations of the markers and yields than the other methods.

3.5 Volume/Time/Frequency Analysis (ABC)

An orthogonal test was devised to determine the optimum Volume/Time/Frequency for the extraction. The results (not shown) indicated that only frequency had a significant effect and accordingly reflux was repeated. The selected criteria were to use 8 folds of ethanol, to reflux for 1 hour and to repeat the process 3 times.

3.6 Purification

The optimum purification conditions after the oils were removed with centrifugation were determined to be as follows:

3.6.1 Conduct separation and purification with column filled with $D_{101}$ Macroporous Resin;

3.6.2 Employ a column ratio (diameter to height) of 1:20;

3.6.3 Add the sample to the column with a dynamic absorption of less than 1.4 BV (BV: resin bed volume) preferably at a speed of 1 BV/h.

3.6.4 Wash with 2 BV of water and then with 4 BV of 20% ethanol at a speed of 2 BV/h (This step is used to remove water soluble gums);

3.6.5 Elute with 4 BV of 70% ethanol at a speed of 2 BV/h and collect 70% ethanol solution;

3.6.6 Recover ethanol and dry the residue under vacuum;

3.6.7 Dissolve the extract in 95% ethanol. Filter and recover the ethanol from the solution under vacuum;

3.6.8 Dry the residue at 60° C. and pulverize to a desired particle size.

Fuller details and evidence supporting the selection of the above conditions are given below:

3.7 Selection of Resin

Both static and dynamic absorption ability was investigated in several resins. The selection criteria were the absorption and desorption efficiency of the resins.

3.7.1 Pre-Treatment of Resin

Clean the column to prevent contamination. Add half of the resin volume of 95% ethanol into the column first, and then fill the column with macroporous resin. The level of ethanol solution should be 0.3 meter above the resin bed top. Leave the ethanol solution in the column for 24 hours.

Use 2 BV (2 folds of Bed Volume of resin in the column, same as below) of 95% ethanol to wash the resin at a speed of 2 BV/h. Leave the solution in the column for a further 4-5 hours. Wash the resin again with 95% ethanol at a speed of 2 BV/h until the eluent shows no cloudiness when diluted with 5 times of water. Then wash the resin with distilled water at the same speed until the eluent does not smell of ethanol.

Use 2 BV of 5% HCl solution to wash the resin at a speed of 4-6 BV/h and leave the solution in the column for 2-4 hours. Use distilled water to wash the resin again at the same speed until the eluent has a neutral pH value.

Use 2 BV of 2% NaOH solution to wash the resin at the speed of 4-6 BV/h and leave the solution in the column for 2-4 hours. Use distilled water to wash the resin again at the same speed until the eluent has a neutral pH value.

3.7.2 Static Absorption Test

Method: The five resins selected were treated to remove surface water.

A quantity of each resin was weighed and put into a stopped flask. The test solution was added to a hyper-saturated status and vibrated for 24 hrs to enable the resin to fully absorb the anthraquinones. Quantify the content of the anthraquinones to evaluate the efficiency of the static absorption ability of the resin.

Filter and obtain filtrate 1. Add 80 ml of 95% ethanol into the resin and vibrate for 24 hrs to desorb the compounds, then filter again and obtain the filtrate 2.

Determine the contents of filtrate 1 and 2 (not given), and calculate the absorption and desorbtion rates. The result are given in Table 8 below

TABLE 8

Table 8. The absorbing and desorbing rate of anthraquinones on macroporous resin in the static absorbing test

| Resins tested | Chemical contents (mg) | Absorbing rate (%) mean | Desorbing rate (%) mean |
|---|---|---|---|
| $D_{101}$ | 1260 | 35.72 | 94.81 |
| X-5 | 1260 | 27.78 | 88.81 |
| NKA-9 | 1260 | 19.05 | 65.45 |
| NKA-12 | 1260 | 21.95 | 95.56 |
| D4020 | 1260 | 21.51 | 61.14 |

It can be seen from Table 8 that the best all round macroporus resin was $D_{101}$ as it was bound relatively efficiently (greater than 30%) and in excess of 90% of the bound material was desorbed.

3.7.3 Dynamic Absorption Test

Method: The eluent from the column was subjected to HPLC. The addition of test solution to the column was stopped when aurantio-obtusin was detected. Record the volume of the test solution added. Wash the column with distilled water until the eluent is nearly colorless and collect the water solution. Then elute with 95% ethanol until the eluent is nearly colorless and collect the ethanol solution. Determine the content of the anthraquinones in these two solutions and calculate the absorption and desorbtion rate, respectively. The results are provided in table 9

TABLE 9

Table 9. The absorbing and desorbing rate of anthraquinones on macroporous resin in the dynamic absorbing test

| Resins tested | Anthraquinones (mg) | Absorbing rate (%) mean | Desorping rate (%) mean |
|---|---|---|---|
| $D_{101}$ | 3360 | 64.28 | 85.12 |
| X-5 | 3360 | 56.38 | 96.87 |
| NKA-9 | 3360 | 27.18 | 54.76 |
| NKA-12 | 3360 | 58.52 | 90.69 |
| D4020 | 3360 | 38.09 | 58.93 |

In the dynamic absorption test D101 resin showed better ability in both absorption and desorbtion than the others. In this regard the absorbing rate was in excess of 60% and the desorbing rate in excess of 80%.

The static and dynamic absorption test results suggested that $D_{101}$ macroporous resin was better than the others so it was selected for separation and purification of the crude extract.

3.8 Investigation of Technical Parameters in the Column Separation and Purification of the Anthraquinones Concentration of the sample application to the column.

Sample solutions with different concentrations (raw material:solution) were flowed through the column filled with 50 g of pre-treated $D_{101}$ resin as for the dynamic absorption test. The absorbed quantity of the anthraquinones was determined. The results are given in Table 10 below.

TABLE 10

Table 10. Absorbed quantities of anthraquinones on $D_{101}$ macroporous resin in different concentration of the *Cassia* extracts

| Sample concentration | Desorping rate (%) mean |
|---|---|
| 1:1 | 47.22 |
| 1:2 | 51.75 |
| 1:5 | 76.66 |
| 1:8 | 76.61 |
| 1:10 | 76.61 |

From the above table it can be seen that the anthraquinones were more easily absorbed to resin when the concentration ratio increased and plateaued at 1:5 (raw material:solution).

3.9.1 Determination of Absorption Flow Speed

The sample solutions were flowed through the column filled with 50 g of pre-treated $D_{101}$ resin at the speeds of 1, 2, 3 BV/ht, respectively, for dynamic absorption test. Elute with distilled water and then 95% ethanol, collect the ethanol solution to determine the content of the anthraquinones.

The results are given in Table 11 below:

TABLE 11

Table 11. The effect of flow speed on the absorption of D101 macroporous resin for *Cassia* extracts

| | Speeds | | |
|---|---|---|---|
| | 1 BV/h | 2 BV/h | 3 BV/h |
| Mean anthraquinone content mg | 2140 | 1970 | 1773 |

The results suggested that the slower the speed, the better the absorption effect. Thus the flow speed of 1 BV/h was selected.

3.9.2 Leakage Curve Determination

The sample solution was flowed through a column filled with 50 g of pre-treated $D_{101}$ resin with the conditions as for the dynamic absorption test. The eluent was collected in 10 ml fractions, and 10 fractions in total were collected. Filter the fractions with 0.2 μm microporous film and determine the content of aurantio-obtusin by HPLC. The result are given in table 12.

TABLE 12

Table 12. Leakage curve of Cassia extracts on D101 macroporous resin.

| | Fractions ml | | | | | | | | | |
|---|---|---|---|---|---|---|---|---|---|---|
| | 10 | 20 | 30 | 40 | 50 (1BV) | 60 | 70 | 80 | 90 | 100 |
| aruantio-obtusin mg | 0 | 0 | 0 | 0 | 0 | 0 | 0 | 45.00 | 96.75 | 97.75 |

From the table above, the leakage started when the sample quantity in the column exceeded 1.4 BV. (ml/g)

3.10 Investigation of the Concentration of the Eluent

The sample solutions were flowed through 4 columns filled with 50 g each of pre-treated $D_{101}$ resin with conditions as for the dynamic absorption test. The 4 columns were eluted with distilled water until the eluent was nearly colorless and then eluted with 30%, 50%, 70% and 90% ethanol. The ethanol eluent was collected. The content of the anthraquinones was determined. The result are given in table 13.

TABLE 13

Table 13. Effect of different concentration of ethanol on the elution of anthraquinones

| | Concentration | | | |
|---|---|---|---|---|
| | 30% | 50% | 70% | 90% |
| Anthraquinones mg | 1587 | 1907 | 2140 | 1733 |

The result showed that the fraction between 50 and 90% ethanol, namely 70% ethanol, had the best elution ability. So 70% ethanol was selected.

3.11 Determination of Elution Speed

The columns were filled with 50 g of pre-treated $D_{101}$ resin and after the dynamic absorption the column was eluted with 70% ethanol at speeds of 1, 2, and 3 BV/h, respectively. The content of the anthraquinones in the ethanol solution was determined. The results are given in table 14.

TABLE 14

Table 14. Effect of different elution speed on the elution ability of anthraquinones

| | Speed | | |
|---|---|---|---|
| | 1 BV/h | 2 BV/h | 3 BV/h |
| Anthraquinones (mg) | 2180 | 2120 | 1960 |

From the table above, it was determined that the slower the elution speed, the better the desorption effect. The difference between 1 BV/h and 2 BV/h was not significant and 2 BV/h was selected in consideration of reducing processing time and increasing efficiency in large scale production.

3.12 Desorption Curve

Based on above selected conditions, apply the sample solution onto a column filled with 50 g of pre-treated $D_{101}$ resin. Elute with ethanol. Collect the ethanol solution with every 10 ml as one sample. After $15^{th}$ sample, collect 20 ml as one sample for further 20 samples. Determine the content of aurantio-obtusin by HPLC and prepare the elution curve. Results are given in table 15.

TABLE 15

Table 15. Desorption curve of aurantio-obtusin in Cassia extracts on $D_{101}$ macroporous resin

| | Sample | | | | | | |
|---|---|---|---|---|---|---|---|
| | 1 | 2 | 3 | 4 | 5 | 6 | 7 |
| Aruantio-obtusin (mg) | 0.76 | 27 | 250 | 281 | 60 | 40 | 26 |

| | Sample | | | | | | |
|---|---|---|---|---|---|---|---|
| | 8 | 9 | 10 | 11 | 12 | 13 | 14 |
| Aruantio-obtusin (mg) | 2.84 | 1.84 | 1.2 | 0.76 | 0.48 | 0.0372 | 0.0276 |

| | Sample | | | | | |
|---|---|---|---|---|---|---|
| | 15 | 16 | 17 | 18 | 19 | 20 |
| Aruantio-obtusin (mg) | 0.0108 | 0.0081 | 0.0062 | 0.0052 | 0.0030 | 0.0040 |

From the table the $18^{th}$ sample showed a very low content of the anthraquinones, so the $18^{th}$ sample (200 ml) was decided as the elution end point, i.e. 4 BV of the eluent to be used.

3.13 pH1 Influence on the Yield of Anthraquinones

The test solution was adjusted to pH 4, 5, and 6 (pH 5 in the original solution), respectively and the effect of pH on anthraquinone content determined—see table 16.

TABLE 16

Table 16. pH influence on the yield of anthraquinones

| | pH value | | |
|---|---|---|---|
| | 4 | 5 | 6 |
| Total chemicals (mg) | 2240 | 2220 | 1740 |

From the table above, the acidic pH of around 4/5 appeared more effective than a pH of around 6.

3.14 The Effect of the Diameter to Height Ratio of the Resin Bed on the Yield of the Anthraquinones Based on the above selected conditions for absorption and elution, 3 columns (20 mm×300 mm) were filled with the pre-treated macroporous resin 17 ml, 34 ml and 50 ml to have a diameter to height ratio 1:5, 1:10, and 1:20, respectively. 1.4 BV of the sample solution was applied to the column and eluted as mentioned. The results are given in table 17.

TABLE 17

Table 17. The effect of the diameter to height ratio of the resin bed on the yield of the anthraquinones

| | Diameter to height ratio of resin bed | | |
|---|---|---|---|
| | 1:5 | 1:10 | 1:20 |
| Group compounds (mg) | 1773 | 1424 | 2081 |

The result showed that when the diameter to height ratio of resin bed was increased above 1:10 to 1:20, the content of the anthraquinones increased.

3.15 Further Purification

There are water soluble gum materials in the *Cassia* seeds. It was found these gums could be dissolved in water and low concentrations of ethanol without eluting the anthraquinones. They could be effectively eluted out by 20% ethanol while anthraquinones could not be eluted out at this concentration. Accordingly a wash step with water followed by elution with 20% ethanol to get rid of the gums was introduced.

In addition, re-dissolving the extract in 95% of ethanol and filtering removed water soluble residues.

3.16 Pilot Scale Production of the Extracts

Based on a process employing the parameters selected above, three batches of pilot scale extractions were conducted in order to confirm the feasibility of the process in the large scale production. The result are given in table 18

TABLE 18

Table 18. Pilot scale production of Cassia extracts

| Batch No | Anthraquinones % | Aurantio-obtusin % | Extract yield % |
|---|---|---|---|
| 030815 | 45.5 | 4.5 | 0.97 |
| 030818 | 51.0 | 5.4 | 1.07 |
| 030821 | 53.4 | 5.8 | 0.98 |
| Average | 50.0 | 5.2 | 1.01 |

A plant extract obtainable by the method described above could be characterized as having an anthraquinone content in excess of 45% and an aurantio obtusin content in excess of 4.5%, measured as and calculated on the basis of the total aglycone after acid hydrolysis. It was subjected to further quality analysis as set out in 4.0 below:

4.0 Quality Specifications

Product Code: PYN 22

This product extracted from the seeds of *Cassia obtusifolia* using ethanol as per the methodology described above was determined to contain a minimum of 4.5% aurantio-obtusin (total of the aglycone in both free form and in combined form which could be made to be free form with hydrolysis), and have a total anthraquinone content of at least 50%. The amount of obtusifolin was at least 0.25%, more typically at least 0.5%. Based on pilot scale averages the anthraquinone content is about 50%, the aurantio-obtusin content is about 5.2% and the obtusifolin content (based on Table 19) is about 0.6% (all figures plus/minus 10%).

It can be characterized by way of HPLC as described under 3.1.1-3.1.4.

Weigh 10 mg sample, add 20 ml of methanol and 10 ml of 5% HCl, and reflux for 30 minutes. Extract the solution with 30 ml ether and remove the ether from the solution. Dissolve the residue in methanol in a 25 ml volumetric flask, shake well and add further methanol to volume. Filter through a 0.22 μm micro membrane before injection.

Inject 20 μl of sample solution, determine peak area of each component, substitute the value in the linear equations to calculate the content, the result is as follows (unit: mg/g):

TABLE 19

| Series No. | Aurantion-obtusin | Obtusifolin |
|---|---|---|
| 1 | 57.599 | 6.785 |
| 2 | 45.178 | 5.231 |
| 3 | 52.433 | 6.189 |
| Average | 51.737 | 6.068 |

Figure 4:
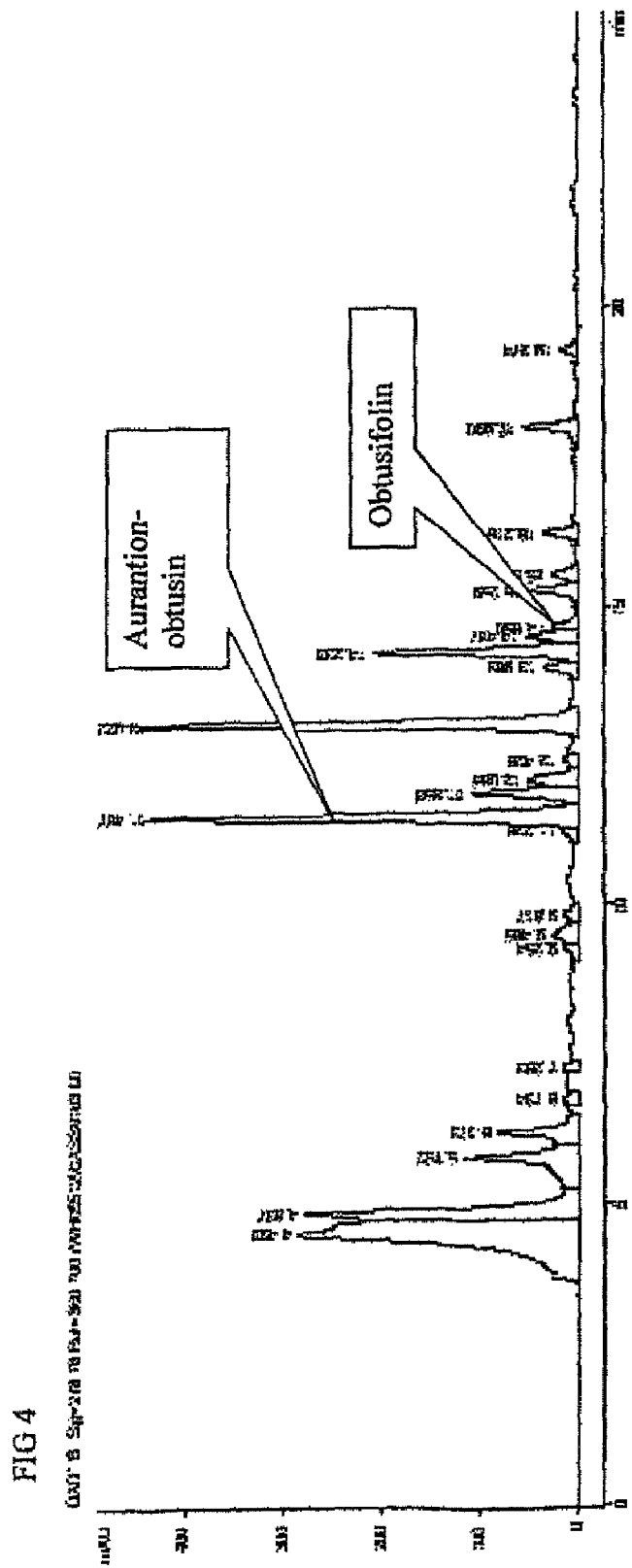
FIG. 4 is an HPLC chromatogram for an extract of the invention.

The HPLC profile is given in FIG. 4.
It can also be viewed by TLC.

Methodology:

Take 10 mg of the 4 batches of the samples, respectively, add methanol 10 ml, under ultrasonic vibration for 60 mins, filter and the filtrate as the sample solution;

Dissolve appropriate amount of Aurantion-obtusin and Obtusifolin in methanol as the reference solution.

Perform TLC based on the methods described in the Chinese Pharmacopoeia (Appendix VI B). Apply 1 μl of each of the above solutions onto a plate. (Activation at 105° C. for 30 mins before use).

Developer:

Petroleum ether (30° C.-60° C.): n-hexane:ethyl formate: formate (1:3:1.5:0.01).

Pre-saturate TLC tank for 15 mins before the plate is put in.
Developed TLC plates.

Figure 5:
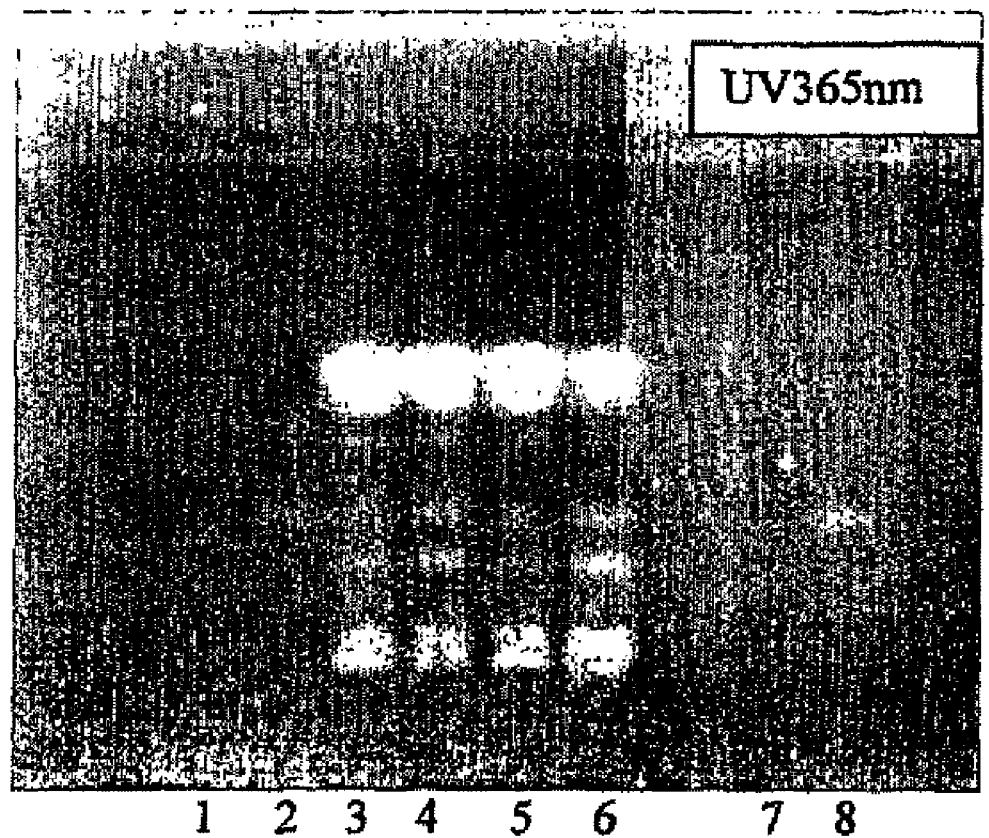
FIG. 5 is a TLC plate of an extract of the invention at 365 nm.
Figure 6:
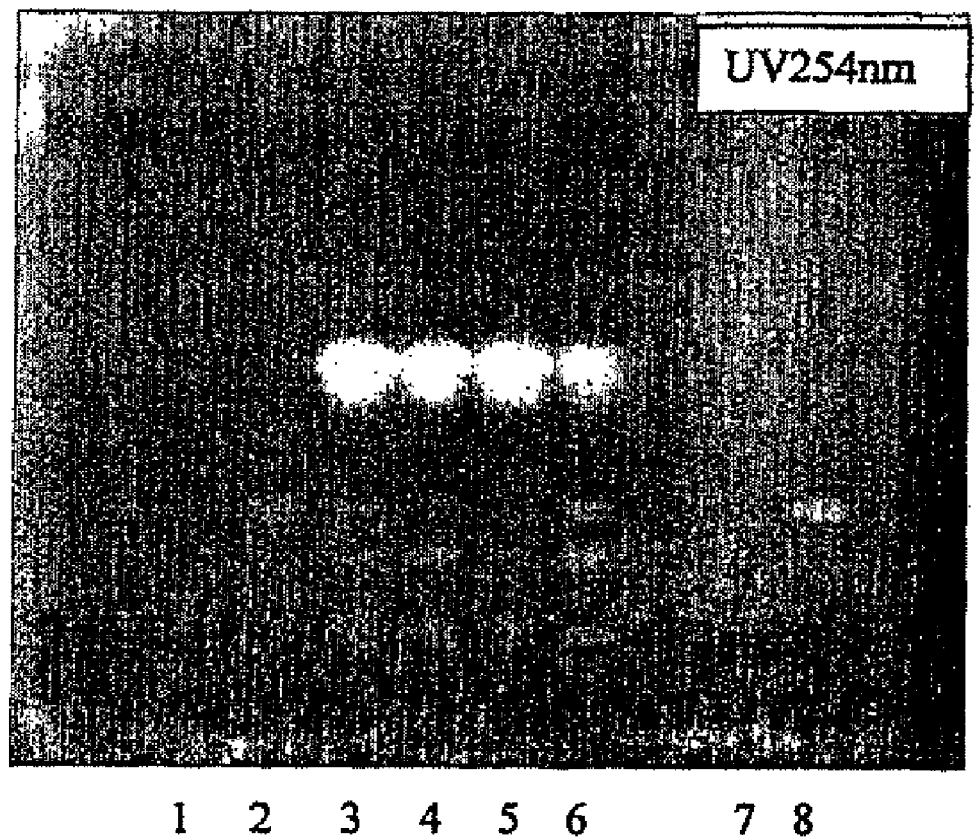
FIG. 6 is a TLC plate of an extract of the invention at 254 nm.

Examine the TLC plates at UV365 nm and 254 nm. The results are illustrated in FIGS. 5 and 6 respectively.

It can be further characterized as follows:

| | |
|---|---|
| 1. Appearance | Brown powder with slightly unique smell. |
| 2. Content of Aurantio-obtusin | >5% (HPLC) measured as and calculated on the basis of the total aglycone after acid hydrolysis |
| 3. Content of obtusifolin | >0.5% (HPLC) measured as and calculated on the basis of the total aglycone after acid hydrolysis |
| 4. Loss on Drying | <9.0% (1 g sample, 105° C., 2 h) |
| 5. Purity Test | |
| (1) Heavy Metals | <10 ppm |
| (2) Arsenic | <1 ppm |
| 6. Microbial counts | <3 × $1^3$ cfu/g |
| 7. Moulds and Yeasts | <1 × $10^3$ cfu/g |
| 8. Coliforms | Negative |
| 9. Composition | 100% *Cassia obtusifolia* extract. |

The dried extract can be used to fill capsules, in a unit dosage form, containing e.g. 250 mg of extract such that a daily does of 500 mg can be easily given. This is equivalent to a 50 g of the raw material.

In animal studies the extract has been demonstrated to exhibit an anti-obesity activity.

5.0 Efficacy Studies

Anti-Obesity Effect
Materials and Methods
Sample:

The sample PYN22 was prepared using the protocol described above. It is a dark brown powder.

Experimental Animals and Feeding Materials:

Seventy five male SD rats, weighting 140 g±10 g each, were provided by the Experimental Animal Centre, Sichuan University. The animal lived in an environment with a temperature of 22-24° C. and a humidity of 65-70%. They were fed on two diets:

i) Basic Feeding Materials: Barley powder 20%, dehydrolized vegetables 10%, bean powder 20%, yeast 1%, bone powder 5%, corn flour 15%, wheat bran 16%, fish powder 10% and salt 2%.

ii) High fat and high nutrition feeding materials: To 100 g of the basic feeding materials were added 10 g milk powder, 10 g lard, one egg, 10 drops of concentrated fish liver oil and 50 g of fresh bean sprouts.

Dose Selection:

Based on a recommended daily dose of 0.5-0.6 g for humans, three doses, 0.05 g/kg·bw/day, 0.15 g/kg·bw/day and 0.30 g/kg·bw/day, were selected for the animal study, which were equivalent to 5 fold, 15 fold and 30 fold of the recommended human daily dose, respectively.
Equipments and Solvents:
   Electronic balance (BL610)
Experimental Methods:
   The rats were randomly divided into five groups:
   1. A normal control group
   2. A high fat control group; and
   3. Three testing groups.
   Each was given the test sample at the dose of 0.05 g/kg·bw/day, 0.15 g/kg·bw/day and 0.30 g/kg·bw/day, respectively.
   The Normal control group was fed with the basic feeding materials. All other groups were fed with high fat and high nutrition materials. All the animals were free to take the food and drink. The test samples were given once a day, via the intragastric route, to the three testing groups at the dose mentioned above (the volume of the liquid was 1% of the body weight of the rat).
   The normal control group and high fat control group were given distilled water instead of the testing sample. The experiment lasted for 36 days. The animals were then dissected.
Observation Criteria:
   Body weight;
   Body fat weight (testis and kidney surrounding fat) and Body fat/body weight ratio were determined and side effects noted.
Data Analysis:
   Statistical software was used for variance analysis.
Results
   The effect on body weight is illustrated in Table 20 below.

TABLE 20

Table 20. The effect of Cassia extract (PYN-22) on the body weight in rats

| | | Body weight (g) | | |
| | Before exp. | Middle term | After exp. | Weight increase (g) |
|---|---|---|---|---|
| Normal control | 15 141.2 ± 9.1 | 222.7 ± 19.3 | 287.7 ± 25.3 | 146.3 ± 29.6 |
| High fat control | 15 141.4 ± 10.9 | 239.7 ± 22.5* | 326.5 ± 37.5** | 184.9 ± 39.1** |
| 0.05 g/kg.bw/d | 15 140.2 ± 10.1 | 223.2 ± 21.7♦ | 293.1 ± 31.1♦ | 152.9 ± 29.1♦ |
| 0.15 g/kg.bw/d | 15 140.7 ± 10.6 | 219.4 ± 32.8♦ | 290.2 ± 39.2♦ | 150.1 ± 36.3♦ |
| 0.30 g/kg.bw/d | 15 139.9 ± 9.9 | 248.9 ± 23.5 | 318.9 ± 51.3 | 179.3 ± 53.7 |

Compared with normal control group:
**$P < 0.01$;
*$P < 0.05$.
Compared with high fat control group:
♦♦$P < 0.01$;
♦$P < 0.05$.

From table 20, the results showed that in the middle term of the experiment, the average body weight of the rats in the high fat control group was significantly higher than that in the normal control group, which meant that the fat animal model was set successfully.

Three groups took the testing materials for 36 days and in two of them, at the dose of 0.05 g/kg·bw/day and 0.15 g/kg·bw/day, their average body weight and increased body weight were significantly lower than that in the high fat control groups, which meant that the testing sample could reduce the animal body weight. No diarrhea and hair loss were observed during the experiment.
The Physical Measurement on the Rat
   The effect on body fat weight is illustrated in Table 21 below.

TABLE 21

Table 21. The effect of Cassia extract (PYN-22) on the body fat weight in rats

| Groups | Animal No. | Final body weight (g) | Body fat wet weight (g) | Body fat/body weight ratio |
|---|---|---|---|---|
| Normal control | 15 | 287.7 ± 25.3 | 6.1 ± 1.7 | 0.022 ± 0.005 |
| High fat control | 15 | 326.5 ± 37.5** | 8.7 ± 2.1** | 0.027 ± 0.006* |
| 0.05 g/kg.bw/d | 15 | 293.1 ± 31.1♦ | 6.5 ± 1.5♦♦ | 0.022 ± 0.006♦ |
| 0.15 g/kg.bw/d | 15 | 290.2 ± 39.2♦ | 6.1 ± 1.9♦♦ | 0.021 ± 0.005♦♦ |
| 0.30 g/kg.bw/d | 15 | 318.9 ± 51.3 | 7.2 ± 2.6 | 0.022 ± 0.006♦ |

Compared with the normal control group: **$P < 0.01$.
Compared with the high fat group: ♦♦$P < 0.01$; ♦$P < 0.05$.

From the table 21 above it can be seen that, at the completion of the experiment, both the body fat content, and body fat/body weight ratio of the high fat control group were significantly higher than that in the normal group ($P<0.01$). This demonstrates that the fat animal model was set successfully.

The body fat content in two testing groups (0.05 g/kg·bw/day and 0.15 g/kg·bw/day) was significantly lower than that in the high fat control group ($P<0.01$);

The body fat/body weight ratio in all three testing groups was significantly lower than that in the high fat control group ($P<0.05$). This demonstrated that the test sample could reduce the body fat content of the animals, i.e. it may act as an anti-obesity agent.
Conclusion
   The body weight, body fat content, body fat/body weight ration in high fat control group were significantly higher than that in the normal control group.

The body weight, body fat content in two testing groups (0.05 g/kg·bw/day, 0.15 g/kg·bw/day) was significantly lower than that in the high fat control group (P<0.01).

The body fat/body weight ratio in all three testing groups was significantly lower than that in the high fat control group (P<0.05).

All results suggested that the test sample had an anti-obesity effect in rat.

6.0 Toxicity Study 6.1 Acute Toxicity Study

The maximum dose of intra-gastric administration of the extract of Cassia-seeds was 16.50 g/kg in a single dose. The $LD_{50}$ was 20.84 g/kg when administrated twice (interval 4 hours) and it was equivalent to 2511 times of proposed clinical dose (kg/bw). So it is safe for adult to take 0.5 g Cassia extract (PYN-22) in two capsules, equivalent to 50 g raw material, per day.

6.2 Long Term Toxicity Study

The rats were intragastrically given the extract of Cassia seed and the rats were dissected in the $16^{th}$, $26^{th}$ week of the medication, and the $4^{th}$ week after the medication, respectively. There were no obvious histopathological changes in the organs from the testing group animals compared with those from the animals in the normal control group.

7.0 Further Experimental Analysis to Consider: a) Body Weight and Body Fat; b) Metabolic Parameters; and c) Liver Indicators Experimental design: Forty C57 black ob/ob mice were allocated to five groups of eight for study over 40 days as follows:

Lean diet—no treatment;
High fat diet—no treatment;
High fat diet—100 mg/kg/OD PYN22;
High fat diet—300 mg/kg/OD PYN22;
High fat diet—3 mg/kg/OD Rosiglitazone (positive control).

Mice were weighed twice per week and food intake measured daily throughout the study. Any laxative effects of treatments were visually examined and recorded.

Oral glucose tolerance tests were conducted on Day 7, Day 21 and Day 35.

Energy expenditure was measured at Day 14.

Fasting plasma insulin and lipids were measured on Days 7, 21 and 35.

Three days before sacrifice, 100 ul blood samples were taken from all animals to provide plasma glucose, insulin, free fatty acid, triglycerides, cholesterol and HDL-cholesterol.

At sacrifice, body mass and fat mass were calculated; the same parameters were also calculated for liver, heart and white adipose tissues.

Animal well-being/safety measures: All animals in each of the study group survived the treatment regimens until the scheduled sacrifice date. Each group of animals was examined on a daily basis and no laxative effect was recorded in any treatment group.

Figure 7A:
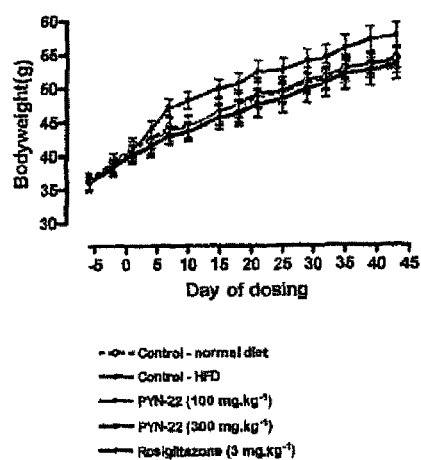
FIG. 7A is a graph showing the effect of PYN22 on weight.
Figure 7B:
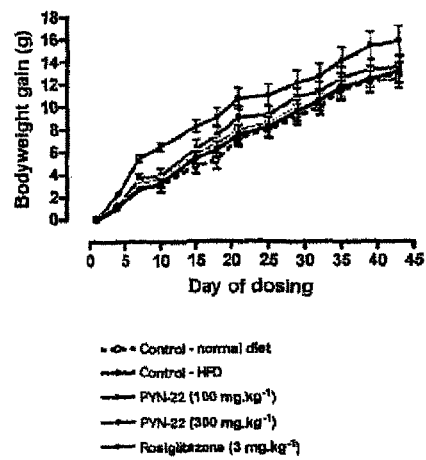
FIG. 7B is a graph showing the effect of PYN22 on weight gain.
Figure 7C:
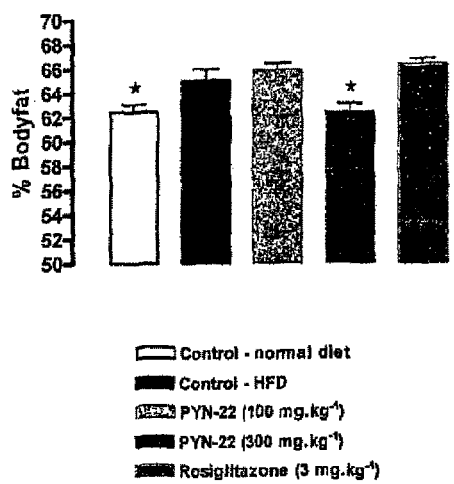
FIG. 7C is a graph showing the effect of PYN22 on body fat.

Data Analysis:

Body Weight & Body Fat:

Over the course of the study, animals in the Rosiglitazone control group had an increased body weight that exceeded the other four groups (FIG. 7A), as reflected clearly in weight gain in the study period (FIG. 7B). However, the body fat gained was not significantly different than the treatment free high fat group. Only high levels of PYN22 resulted in significantly less body fat gain relative to the high fat control, and 300 mg OD PYN22 seemed to prevent body fat increasing above lean control levels, despite high fat intake in this group (FIG. 7C).

In terms of circulating lipids, there was a possible dose-response trend of cholesterol reduction by PYN22 but only Rosiglitazone gave a statistically significant reduction on total cholesterol in high fat diet groups (FIG. 8A). However, 100 mg OD PYN22 gave a significant reduction in HDL cholesterol that became highly significant at 300 mg OD and surpassed the effects of Rosiglitazone (FIG. 5B).

Figure 9A:
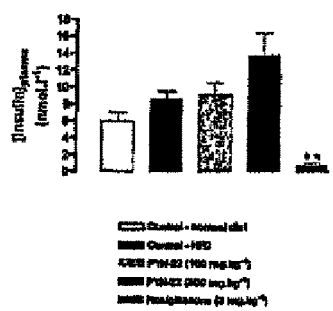
FIG. 9A is a graph showing Fasting insulin levels at day 7.
Figure 9B:
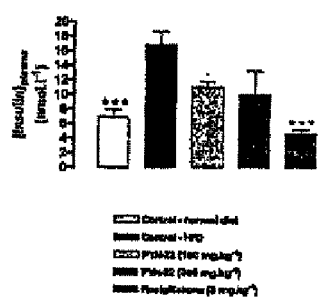
FIG. 9B is a graph showing Fasting insulin levels at day 21.
Figure 9C:
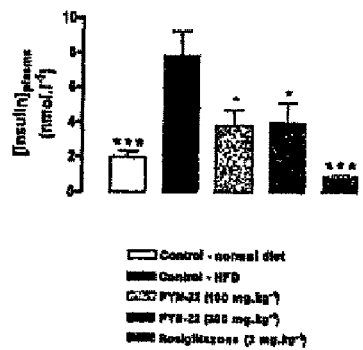
FIG. 9C is a graph showing Fasting insulin levels at day 35.

Metabolic Parameters:

In terms of insulin levels, PYN22 consistently lowered fasting insulin in animals on a high fat diet, bringing levels part-way towards those receiving a lean diet, but not achieving the effects of Rosiglitazone, a marketed anti-diabetic therapy. (FIGS. 9A-9C).

Figure 10A:
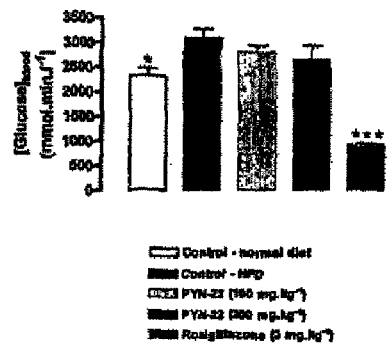
FIG. 10A is a graph showing Oral Glucose Tolerance Tests (AUC) at day 7.
Figure 10B:
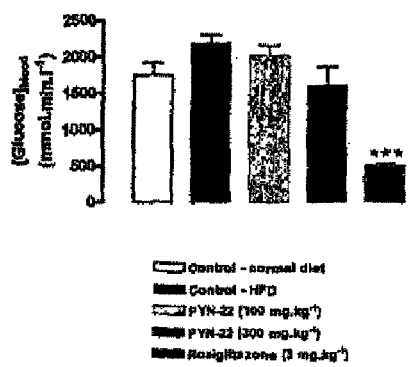
FIG. 10B is a graph showing Oral Glucose Tolerance Tests (AUC) at day 21.
Figure 10C:
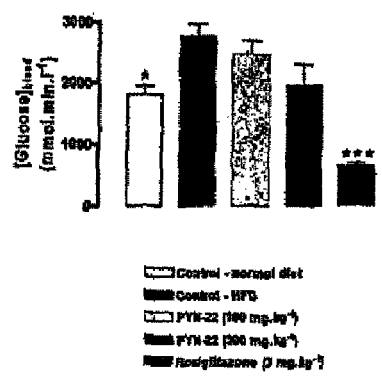
FIG. 10C is a graph showing Oral Glucose Tolerance Tests (AUC) at day 35.

In oral glucose tolerance tests (OGTTs), PYN22 reversed the effects of the high fat diet towards the lean diet group (FIGS. 10A, 10B and 10C) in a dose-dependent trend at all time points in the study but without statistical significance, and with less effect than Rosiglirazone.

Figure 11A:
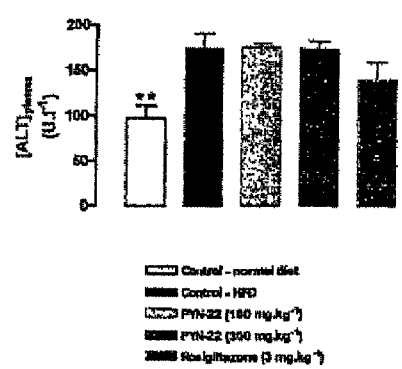
FIG. 11A is a graph showing the effects of PYN22 on liver indicators at day 43—inflammatory markers—ALT.
Figure 11B:
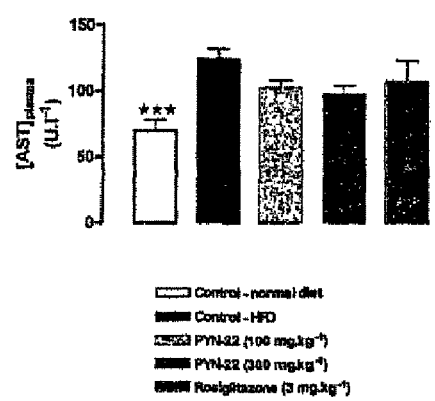
FIG. 11B is a graph showing the effects of PYN22 on liver indicators at day 43—inflammatory markers—AST.
Figure 11C:
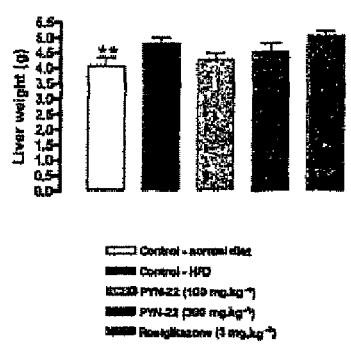
FIG. 11C is a graph showing the effects of PYN22 on liver indicators at day 43—inflammatory markers—liver weight.
Figure 11D:
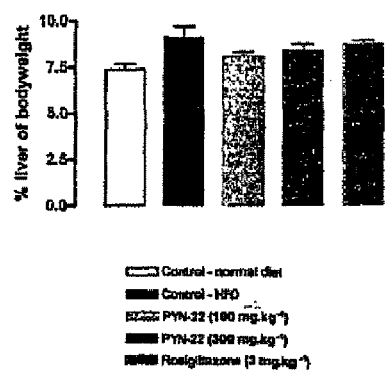
FIG. 11D is a graph showing the effects of PYN22 on liver indicators at day 43—inflammatory markers—as percent body weight.

Liver Indicators:

PYN22 had no effect on ALT levels (but reduced AST levels in a dose-dependent trend but without statistical significance—FIGS. 11A and 11B). PYN22 also reduced actual and relative (% body weight) liver weight,—(FIGS. 11C and 11D) whereas Rosiglitazone had no effect.

Figure 11E:
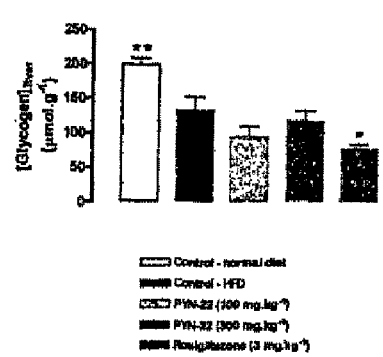
FIG. 11E is a graph showing the effects of PYN22 on liver indicators at day 43—inflammatory markers—liver glycogen.
Figure 11F:
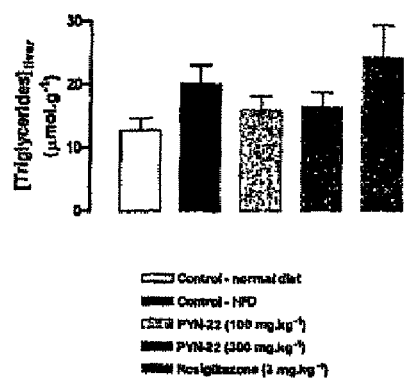
FIG. 11F is a graph showing the effects of PYN22 on liver indicators at day 43—inflammatory markers—tri-glyceride content.

PYN22 had little effect on liver glycogen levels (FIG. 11E) but reduced liver triglycerides substantially (FIG. 11F), although not significantly.

The above results provide credible evidence that in addition to treating obesity the extract of the invention may also be used to treat metabolic disease or liver disease.

Summary

The effect on lipid levels and on metabolic indicators is manifest in a statistically significant reduction in body fat.

The data is additional suggestive of further clinical application in the treatment of:

Chronic inflammation of the liver resulting from metabolic overload and fat deposition;
Fatty liver; and
Fibrogenesis.

The invention claimed is:

1. A therapeutically effective amount of an alcohol extract composition of *Cassia obtusifolia* seeds or *cassia tora* seeds for use in the treatment of obesity and related metabolic and liver diseases comprising:
   i) at least 2% aurantio-obtusin as determined by hplc analysis;
   ii) at least 0.2% obtusifolin as determined by hplc analysis;
   iii) at least 25% total anthraquinone glycoside as determined by spectrophotometry;
   iv) said aurantio-obtusin and said obtusifolin being present in a ratio between 5:1 and 30:1; and
   said extract being absent of lipo-soluble gums and water soluble gums and being selectively purified by at least a factor of 50 as compared to unextracted *Cassia obtusifolia* seeds or *cassia tora* seeds.

2. The extract composition of claim 1 comprising at least 5% aurantio-obtusin by hplc analysis.

3. The extract composition of claim 2 comprising at least 10% aurantio-obtusin by hplc analysis.

4. The extract composition of claim 1 comprising about 0.5% obtusifolin by hplc analysis.

5. The extract composition of claim 1 wherein the ratio of aurantio-obtusin to obtusifolin is between 8:1 and 16:1.

6. The extract composition of claim 1 wherein the total anthraquinone comprises chrysophanol, physcion, obtusifolin, emodin and aurantio-obtusin.

7. The extract composition of claim 1 comprising at least 45% total anthraquinone by spectrophotometry.

8. The extract composition of claim 1 which has been purified by at least a factor of 75 as compared to unextracted *Cassia obtusifolia* seeds or *cassia tora* seeds.

9. The extract composition of claim 1 which is an ethanol extract.

10. The extract composition of claim 9 which is a refluxed extract.

11. The extract composition of claim 1 which is in a unit dosage form.

12. The extract composition of claim 11 wherein the unit dosage form is a capsule for oral delivery.

13. The extract composition of claim 11, wherein the unit dosage form comprises 50-5000 mg of extract which is equivalent to 5 to 500 g of unextracted *Cassia obtusifolia* seeds or *cassia tora* seeds.

14. The extract composition of claim 13 wherein the unit dosage form is a dietary supplement, food stuff or cosmetic.

* * * * *